(12) United States Patent
Kutzner et al.

(10) Patent No.: US 8,512,606 B2
(45) Date of Patent: Aug. 20, 2013

(54) PROCEDURE FOR DIMENSIONALLY ACCURATE SINTERING OF A SHAPED PIECE

(75) Inventors: Martin Kutzner, Neuberg (DE); Sarah Tullney, Darmstadt (DE)

(73) Assignee: Degudent GmbH, Hanau (DE)

( * ) Notice: Subject to any disclaimer, the term of this patent is extended or adjusted under 35 U.S.C. 154(b) by 862 days.

(21) Appl. No.: 12/504,726

(22) Filed: Jul. 17, 2009

(65) Prior Publication Data
US 2010/0015570 A1 Jan. 21, 2010

(30) Foreign Application Priority Data

Jul. 18, 2008 (DE) .......................... 10 2008 002 952

(51) Int. Cl.
*A61C 13/00* (2006.01)
(52) U.S. Cl.
USPC ............................................ 264/16; 264/138
(58) Field of Classification Search
USPC .................................................. 264/138, 16
See application file for complete search history.

(56) References Cited

U.S. PATENT DOCUMENTS

| | | | |
|---|---|---|---|
| 7,077,391 B2 * | 7/2006 | Filser et al. | 269/287 |
| 2006/0082033 A1 | 4/2006 | Hauptmann et al. | |
| 2007/0108645 A1 | 5/2007 | Von Schroeter et al. | |
| 2010/0323327 A1 * | 12/2010 | Eriksson et al. | 433/199.1 |

FOREIGN PATENT DOCUMENTS

| | | |
|---|---|---|
| EP | 1 154969 | 11/2001 |
| WO | 99 47065 | 9/1999 |
| WO | 02 45614 | 6/2002 |
| WO | WO 2004/086999 | 10/2004 |
| WO | 2005 051220 | 6/2005 |

OTHER PUBLICATIONS

"Zirkonzahn", 2004, pp. 49-56.
Wieland, Leitfaden zur Konstruktiion and Verarbeitung von ZENO Zr gerusten, 2006.
Quintessenz Zahntech 2006, pp. 682-693.
Zirkonzahn: A. Kanotscher: Zirkon-Fras—oder Glas-Presskeramik.

* cited by examiner

*Primary Examiner* — Galen Hauth
(74) *Attorney, Agent, or Firm* — Ladas & Parry, LLP

(57) ABSTRACT

A procedure for dimensionally accurate sintering of a shaped piece manufactured from a blank of porous ceramic material, in which during the sintering, the shaped piece remains connected via at least one first connection like a rib, with a support that is manufactured from the blank. To ensure with simple procedural steps and simple design measures that the geometry does not change during sintering, the invention provides that the support is manufactured as a section of the blank that at least in sections surrounds the shaped piece by materials removal processing from the blank, and after the manufacture, the support, for one, is connected via the at least one first connection with the shaped piece, and for another, via at least one second connection with the residual blank that in sections is separated from the support.

15 Claims, 3 Drawing Sheets

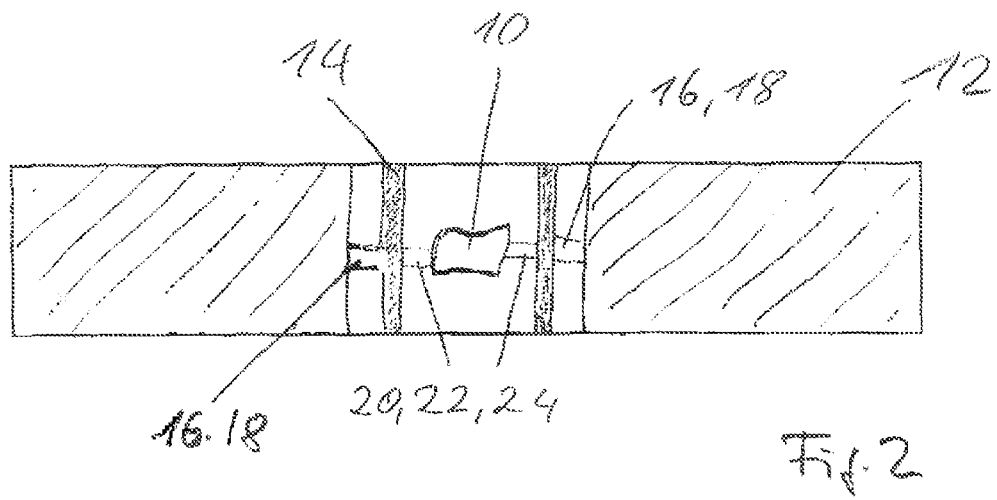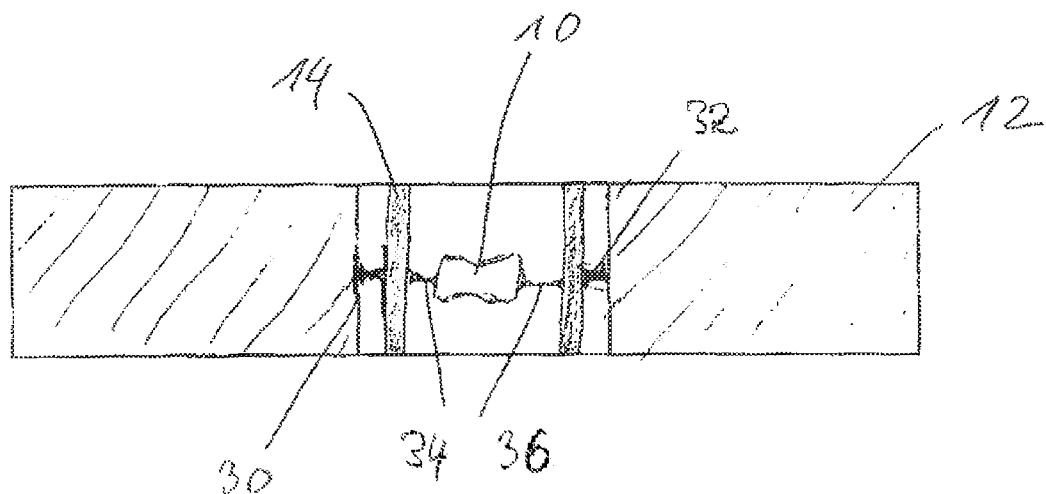

PROCEDURE FOR DIMENSIONALLY ACCURATE SINTERING OF A SHAPED PIECE

BACKGROUND OF THE INVENTION

The invention relates to a procedure for dimensionally accurate sintering of a shaped piece manufactured from a blank consisting of a porous ceramic material, especially a dental bridge, in which the shaped piece during sintering remains connected with a support via at least a first connection like a rib, which is manufactured from the blank. The invention also makes reference to a residual blank as a part of a blank consisting of a porous ceramic material with a shaped piece manufactured by removal of material from the blank that is connected integrally with the residual blank.

A procedure of this type is known from EP-B-1 154 969. To prevent during sintering of the shaped piece, which consists of a ceramic material, movement of the shaped piece relative to a base due to the reduction in volume (shrinkage), provision is to brace the shaped piece on a movable support such as a holding rib or on rollers. The possibility also exists to connect the shaped piece and the rib projecting in integral fashion from it with a burner base that is manufactured together with the shaped piece from a blank by materials removal. With a bridge having multiple members, from each bridge member a rib projects outward.

This has a disadvantage in that if the base is deformed, the alteration in geometry can be transferred to only one of the members, with the possibility that the members can move relative to each other, and the shape can change in undesired fashion.

WO-A-99/47065 and WO-A-02/45614 relate to dental bridges that are manufactured through sintering from blanks consisting of porous ceramic material. For this, the blank is accommodated by a frame to produce the bridge by milling. First the bridge is connected via ribs with the residual blank remaining from the blank, which ribs are separated when the processing is completed. The separation spots are then ground smooth. Then the sintering takes place.

From WO-A-2005/051220, a procedure is known for manufacturing a crown as a shaped piece. With this procedure, the shaped piece is processed out of a blank, and before releasing the shaped piece from the blank, it remains connected to the residual blank via one or more ribs, which then are cut through. Then a sintering through occurs.

SUMMARY OF THE INVENTION

The task constituting the basis of the present invention is to advance a process as well as a unit to be sintered of the type mentioned initially so that with simple procedural steps and simple design measures, it is ensured that when the shaped piece is sintered from the porous ceramic material, the geometry does not change.

According to the procedure, the problem essentially is solved in that the support is manufactured as a section of the blank that at least partially surrounds the shaped piece through a materials removal process, whereby the support on the one hand is connected via at least one first connection with the shaped piece, and secondly is connected via at least one second connection with the residual blank that at least partially surrounds the support with an interval.

Provision is made in particular that the support is manufactured in such a way through materials removal processing, especially by milling of the blank, that the support surrounds the shaped piece in encircling fashion and is processed out, such as by milling, from the blank so that the support, for one, is connected via a first membrane and/or via at least two first ribs with a shaped piece, and, for another, is connected with the remaining residual blank via a second membrane and/or via at least two second ribs.

As a departure from the state of the art, the shaped piece to be sintered is surrounded in encircling fashion by the support and is sintered together with it, whereby during sintering the support serves as a bracing. By this means it is ensured that the volume is reduced with accurate dimensions, without the shaped piece changing so as to produce a wrong geometry. While doing so, preferably, as mentioned, the support itself serves as a bracing on a base. For this, provision is made that the shaped piece, is retrograde-shaped to at least one section of the support's outer surface, on which the residual blank is positioned on a base during sintering.

Also, however, no departure from the invention occurs if, during sintering, the support remains connected together with the shaped piece and the residual blank, so that the unit in this regard is sintered through in full. With this measure also, it is ensured that the volume is reduced with accurate dimensions, without the geometry becoming wrong; for the residual blank is connected to the support via two connections that are preferably formed by ribs, for example, at specific points.

However, a possibility also exists that the connection is embodied between the shaped piece and the support and/or the connection between the support and the blank in the form of a surrounding membrane or by sections of a membrane. Owing to the thinning of material caused by this, between the elements braced against each other, it is likewise ensured that the shaped piece can be sintered through with accurate dimensions.

Independent of this, provision is made that the support and the shaped piece are connected via multiple first connections like ribs, spaced evenly over the external circumference of the shaped piece. The support is likewise connected via multiple, preferably rib-shaped second connections, with the residual blank, whereby the second connections should likewise be distributed evenly, or essentially evenly, over the circumference.

In addition, the first and second connections should be arrayed to be displaced relative to each other. With this, the number of the second connections may be smaller than that of the first connections.

Based on the invention-specific teaching, the sintering is carried out virtually in suspended fashion, in which especially the support, but if necessary also the residual blank, or sections manufactured from the blank by materials removal processing, serve as bracings during the sintering.

In advancing the invention, provision is made that from the blank, multiple shaped pieces are manufactured, whereby preferably each shaped piece is configured via at least one first connection like a rib with the one from the residual blank, and remains connected to this support, at least part of which is placed at an interval.

If multiple shaped pieces are processed out of the blank, it is also possible, however, that the shaped pieces are connected among each other via connections like ribs or membranes, or sections of membranes, and the shaped pieces altogether are surrounded at least in sections by a support like a frame, which is used as a bracing during sintering.

Provision is especially made that a disk is used as the blank, with a flat side able to be a section on which the remaining residual blank is positioned on the base.

However, preferably the support, i.e., the frame surrounding the shaped piece, is released from the residual blank, to then carry out the sintering-through. While doing so, the support is positioned on a base. The shaped piece and the base are not in direct contact with each other, since in the area of the base the shaped piece is recessed back to the area on which the support rests on the base.

However, it is also possible to use a blank with the geometry of a cylinder or cuboid.

Especially preferred is to manufacture from the blank a dental bridge with at least 7 members as the shaped piece.

Additionally, the invention relates to a residual blank as part of a blank consisting of porous ceramic material with a shaped piece, manufactured by materials removal from the blank, that is connected integrally with to the blank, and characterized in that the shaped piece is connected via at least one first connection with a support manufactured by materials removal from the blank and at least in sections surrounding the shaped piece, which for its part is connected with it at an interval by at least one second connection at an interval to the residual blank. While doing so the shaped piece is contoured back to an outer section of the support or of the residual blank serving as a bracing on a support.

The residual blank and shaped piece are manufactured integrally from the blank and connected via a support that also is produced from the blank. Between the shaped piece and support on the one side, and this and the residual blank on the other side, a first connection and a second connection are provided. In this respect the shaped piece is integrally connected with the residual blank.

However, for sintering, preferably the residual blank is separated from the support, so that the support-and-shaped-piece unit is sintered or sintered through.

Provision is especially made that the support surrounds the shaped piece at a distance and is connected with it via at least two first connections like ribs. Preferably the support has the geometry of a frame whose shape follows the outer contour of the shaped piece.

The support itself is connected via at least two first and two second connections with the shaped piece or the residual blank, whereby the first and second connections are displaced to each other.

Especially, provision is made that at least the first connections are connected with the support in evenly spaced fashion along the outer contour of the shaped piece.

Preferably the shaped piece is a dental shaped piece such as a multi-member bridge, especially one with at least 7 members.

Additionally, depending on the size of the blank, there is a possibility that the residual blank has multiple shaped pieces as integral component parts.

Instead of ribs which should make possible a connection at specific points between the shaped piece and the support, a connection can also be produced in the form of a membrane by milling, whereby the membrane connects the shaped piece by encircling or alternatively connects the form piece with the support in sectional fashion.

Ceramic materials must be used to a great extent, to produce a shaped piece like a dental bridge. With this, green compacts or pre-sintered blanks are used, since it is relatively simple to process them. After manufacture of the shaped form, it must be sintered through. Since a shaped piece manufactured from the blank is enlarged in linear fashion by an expansion factor in all spatial directions exactly compensating for the sintering shrinkage that follows, it must be ensured that during sintering there is no distortion.

To enable dimensionally correct sintering, according to the invention the blank, which can be a green compact or a pre-sintered body or may consists of a porous ceramic material, is mounted in a machine tool and than processed by materials removal, especially by coarse and/or fine milling.

The blank can be one consisting of a metal oxide power of the group consisting of $Al_2O_3$, $TiO_2$, MgO, $Y_2O_3$ and the zirconia mixed crystal $Zr_{1-x}Me_xO_2(4n/2)_x$, in which Me is a metal that is present in the oxide form as a di-, tri-, or quadravalent cation, and stabilizes the tetragonal and/or the cubic phase of the zirconia. With the formula for the zirconia mixed oxide crystal, n=2, 3 or 4, and $0 \leq x \leq 1$.

The data needed for milling are transmitted via the control electronics of the machine tool and suitable tool paths are derived therefrom. To obtain the signals, customarily a model is digitized beforehand, or data are taken from a library. In this respect, reference is made to techniques adequately known, such as those described in WO-A-1999/47065 or WO-A-2002/45614. Reference is expressly made to the disclosure that concerns this.

BRIEF DESCRIPTION OF THE DRAWINGS

Further particulars, advantages and features of the invention are derived not merely from the claims, the features to be gleaned from same—as such and/or in combination, but rather also from the following description of the preferred embodiment examples to be gleaned from the drawings.

Shown are:

FIG. 2 a section through a residual blank with shaped piece and support according to FIG. 1;

FIG. 3 a section through a residual blank with a shaped piece and support according to a further embodiment form.

DESCRIPTION OF THE PREFERRED EMBODIMENTS

A clarification is made using the figures that from a preferably disk-shaped blank, a shaped piece, which in the embodiment example is a multi-member bridge 10, can be manufactured with no danger of surface distortion. Each member is to be viewed as a dental unit sintered through.

With the specification of embodiment examples that follow, fundamentally the same reference symbols are used for the same elements.

Figure 1:
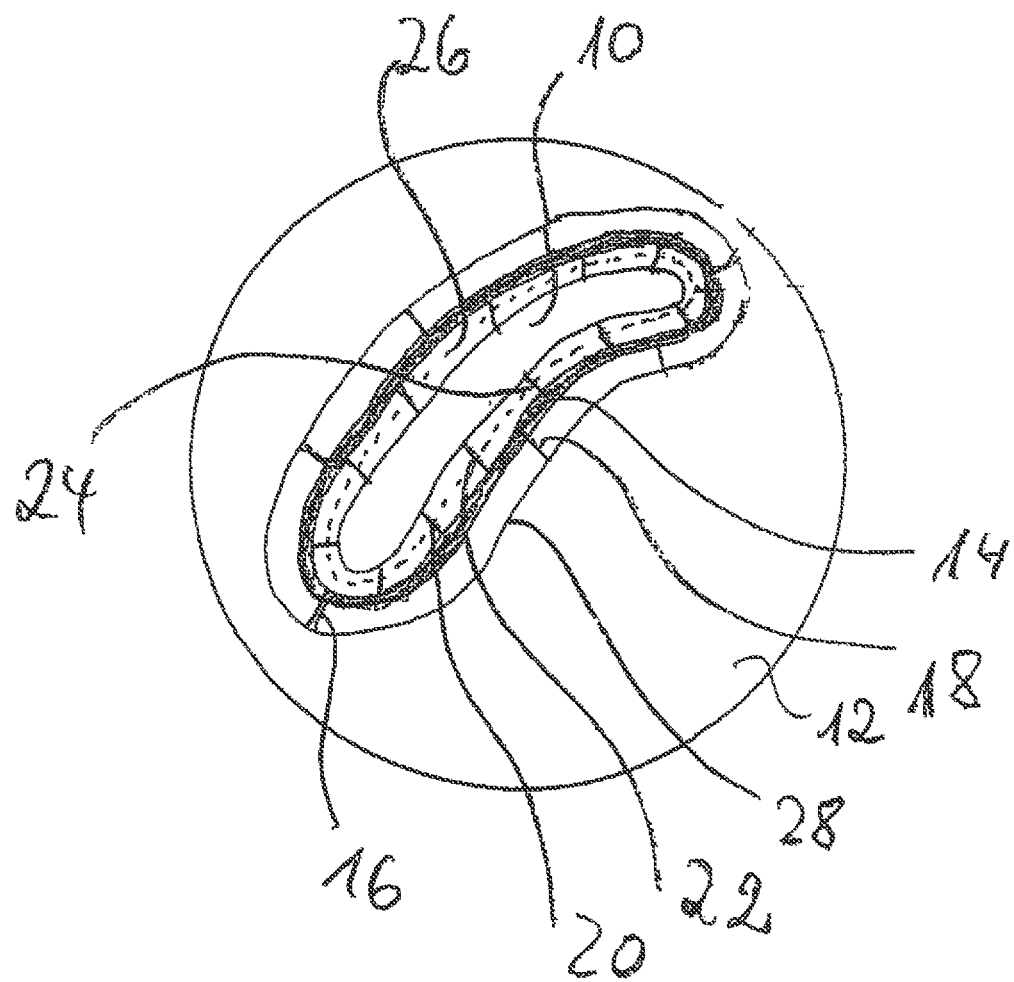
FIG. 1 a residual blank with shaped piece and support in a top-down view.

FIG. 1 shows a top-down view of a residual blank 12, i.e., the part that remains from the original blank after the shaped piece, a frame 14 surrounding it and forming a support, as well as connections that connect frame 14 for one with shaped piece 10 and for another with residual blank 14, which have been processed out by materials removal. The blank can be pre-sintered or be a green compact. However, the invention is also applicable if no pre-sintering occurs.

In the embodiment example of FIGS. 1 and 2, the connections are embodied as ribs 16, 18, 20, 22, 24. However, this is not to be understood as restricting the protection. Connections can also be implemented through surrounding membranes or sections of membranes or combinations of membranes and ribs or connecting elements having the same effect, as shown in FIG. 3. In what follows, for reasons of simplicity, we speak of ribs, even if, as mentioned, other connections that are considered are to be subsumed hereunder.

According to the invention, first the shaped piece 10 and then the frame 14 are manufactured by milling, with the ribs 16, 18, 20, 22, 24 remaining, and at least the frame 14 and the shaped piece 10 can then be sintered as a unit. For this, at the outset it is required that frame 14 be released from the residual blank 12 by cutting through the ribs 16, 18.

Also, however, no departure from the invention occurs if residual blank 12 is sintered as a unit with frame 14 and shaped piece 10.

The frame 14 may have the full height of the disk of the blank, and therefore that of residual blank 12. In contrast to that, the sides of shaped piece 10 that run parallel to the flat sides of the support or of frame 14 or of residual blank 12 run at a distance to them, or at least the outer side of shaped piece 10, which faces the side on which support 14 or residual blank 12 lies during sintering, runs contoured back thereto.

Naturally, frame 14 also can be contoured back if a sintering together with the residual blank 12 is carried out.

The geometry of the frame 14 is computed as follows: the geometry of the frame 14 is computed starting from the central encircling path of the coarse milling cutter about the geometry of the shaped piece; from it, the milling cutter is projected outward in encircling fashion by a value computed from the milling cutter radius+distance value+frame thickness+milling machine radius.

The frame 14 may be 1 mm to 10 mm wide, but preferably 2 mm to 3 mm. The height of the frame 14 includes the height of the blank used, and may also deviate from that under certain milling conditions for manufacturing the bridge.

The distance between frame 14 and the bridge or shaped piece 10 should be equal to twice the milling cutter radius plus a distance value of 0.1 mm to 0.3 mm.

As can be seen from FIG. 1, the ribs 16, 18, 20, 22, 24 running between shaped piece 10, which is the multi-member bridge, and frame 14, should be placed to be evenly distributed over the circumference of shaped piece 10. The number of the ribs 20, 22, 24 by which shaped piece 10 is connected with frame 14, is preferably larger than the number of ribs 16, 18 that extend from frame 14 and terminate in the edge 28 of residual blank 12 that surrounds frame 14 in encircling fashion. Additionally, the ribs 16, 18 between frame 14 and residual blank 12 are to connect to the ribs 20, 22, 24 that connect frame 12 to shaped piece 10 are displaced from each other, to make possible a desired capacity of shaped piece 10, frame 14 and residual blank 12 to be relatively shifted, by which sintering is ensured with accurate dimensions.

The distance between frame 10 and the surrounding edge 28 of the blank is to be selected in dependence on the geometry of the bridge to be manufactured, i.e., of the shaped piece, and can be between 0 mm and 30 mm, preferably between 0 mm and 3 mm. The latter makes possible a good exploitation of the available blank surface. 0 mm means that the outer edge of the support or of frame 14 is equal to the section of the surrounding surface of the blank itself.

Regarding ribs 16, 18, 20, 22, 24, it is to be noted that they can have a round or an oval cross section. The cross section per rib should be between 0.5 mm$^2$ and 13 mm$^2$, preferably between 1 mm$^2$ and 3 mm$^2$.

The ribs 20, 22, 24 are to be attached to shaped piece 10 at the largest cross section of the particular dental unit, but not at the adjustment edge of a particular crown.

The number of ribs per dental unit is from 0 to 2, preferably 1. With a multi-member bridge, consequently, not every member or dental unit must be connected via a rib with the frame. If shaped piece 10 consists of a single dental unit, then the number of ribs is at least 2.

Alternatively, it is possible to connect frame 14 with shaped piece 10 via a membrane that has a thickness between 0.1 mm and 1 mm, and is preferably in the range between 0.3 mm and 0.5 mm. As an alternative, connections can also be produced from partial sections of a membrane which, in the circumferential direction of shaped piece 10 should have lengths between 0.5 mm and 5 mm, preferably between 1 mm and 3 mm.

Owing to the selected design, the shaped piece 10 is sintered virtually in suspended fashion. After shaped piece 10 is sintered through, ribs 20, 22, 24 are separated from shaped piece 10 and the lugs, if necessary, are re-processed.

In the embodiment example, if a single shaped piece 10 is manufactured from the blank, then a possibility very readily exists to produce multiple shaped pieces simultaneously in the blank, which in the manner described above, are connected via one or more connections like ribs with supports, which for their part are placed at intervals via further connections like ribs to the remaining residual blank. In this manner, a separate frame can be assigned to each shaped piece, or multiple shaped pieces to a common frame.

One can perceive from the drawing that the frame 14 essentially runs parallel to the outer contour of shaped piece 10. Additionally, the distance between frame 14 and shaped piece 10, i.e., the areas that face each other, should have an interval that is not much greater than the effective diameter of the tool used, such as a milling cutter. The same holds true regarding the distance between the circumferential surface of frame 14 and the limiting edge 28 of residual blank 12. The edge 28 has a shape that preferably follows the outer or circumferential contour of frame 14.

In the embodiment example, if the support for shaped piece 10 is to be described as a frame 14, the invention is not restricted thereby. Rather, other configurations or geometries are also possible and included by the invention.

FIG. 2 corresponds to the basis of FIG. 1, and consequently represents a section through residual blank 12, but with changes occurring regarding the geometries in comparison to FIG. 1. Notwithstanding, ribs 16, 18, 20, 22, 24 are drawn in on principle, via which shaped piece 10 is connected with the support or frame 14 respectively, and this is connected with residual blank 12.

By comparing FIGS. 1 and 2, it can be seen that the blank is a disk.

As was previously explained, the connection between shaped piece 10 and support 14 and between same and residual blank 12 is produced not merely via ribs 16, 18, 20, 22, 24 but also via membranes or sections of membranes, was can be gleaned in principle from the sectional depiction of FIG. 3. Thus, shaped piece 10 is connected via membranes or sections of membranes 34, 36 with the support, which is connected on its side via membranes 30, 32 or sections of same with the residual blank 12.

Figure 4:
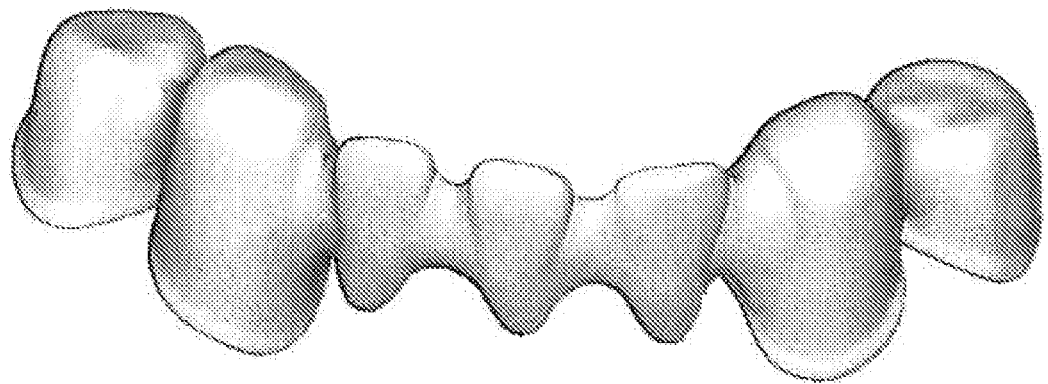
FIG. 4 a 7-member bridge.

In addition, as to FIG. 4, a 7-member bridge 38 may be inferred, which has been produced using the invention-specific procedure.

What is claimed is:

1. A method for dimensionally accurate sintering of a shaped piece (10) manufactured from a blank comprising porous ceramic material, whereby during the sintering the shaped piece remains connected via at least one first connection (20, 22, 24) to a support (14) that is manufactured from the blank, characterized in that the support (14) is manufactured as a section that at least in sections surrounds the shaped piece (10) by materials removal processing from the blank, whereby the support, first, is connected via the at least one first connection (20, 22, 24, 34, 36) with the shaped piece, and second, via at least one second connection (16, 18, 30, 32) with the residual blank (12), wherein said residual blank surrounds the support and is at least partly spaced from the support.

2. A method according to claim 1, wherein the support (14) surrounds the shaped piece (10) in encircling fashion and is processed or milled out of the blank so that, first, the support is connected via a first membrane (34, 36) or sections of the first membrane and/or via at least two first ribs (20, 22, 24) with the shaped piece and, secondly, with the remaining residual blank (12) via a second membrane (30, 32) or section of this, and/or via at least two second ribs (16, 18).

3. A method according to claim 1, wherein at least the shaped piece (10) is contoured back to at least one section of an exterior surface of the residual blank (12) and/or of the support (14), and during sintering, the residual blank is positioned on a base.

4. A method according to claim 1, wherein before the sintering or sintering through, the support (14) with the shaped piece (10) is separated from the residual blank (12).

5. A method according to claim 1, wherein a disk is used as the blank, and wherein the disk has a height that corresponds to a height of the support.

6. A method according to claim 3, wherein both the shaped piece (10) and the support (14) are contoured back to at least the one section of the outer surface of the residual blank (12).

7. A method according to claim 1, wherein from the blank, multiple shaped pieces (10) are manufactured, whereby each shaped piece remains connected via at least one first connection (20, 22, 24, 34, 36) with the support (14) formed from the residual blank (12).

8. A method according to claim 7, wherein each shaped piece (10) is surrounded by a separate support (14).

9. A method according to claim 7, wherein multiple shaped pieces (10) are surrounded by a common support (14).

10. A method according to claim 1, wherein the shaped piece (10) is surrounded by a frame as the support (14), whose contour follows the circumferential contour of the shaped piece.

11. A method according to claim 1, wherein a disk is used as the blank.

12. A method according to claim 1, wherein from the blank, a dental bridge having at least 7-members is manufactured as the shaped piece (10).

13. A method according to claim 1, wherein the blank comprising porous ceramic material is a dental bridge.

14. A method according to claim 1, wherein said at least one first connection is a rib.

15. A method according to claim 7, wherein said at least one first connection is at least one of a rib and a membrane.

* * * * *